(12) United States Patent
Polegato Moretti

(10) Patent No.: US 9,033,492 B2
(45) Date of Patent: May 19, 2015

(54) FRAME FOR GLASSES, MASKS FOR PROFESSIONAL OR SPORTS USE, AND THE LIKE

(75) Inventor: Mario Polegato Moretti, Crocetta del Montello (IT)

(73) Assignee: GEOX S.p.A., Montebelluna (IT)

( * ) Notice: Subject to any disclaimer, the term of this patent is extended or adjusted under 35 U.S.C. 154(b) by 178 days.

(21) Appl. No.: 13/812,686

(22) PCT Filed: Jul. 6, 2011

(86) PCT No.: PCT/EP2011/061434
§ 371 (c)(1),
(2), (4) Date: Apr. 9, 2013

(87) PCT Pub. No.: WO2012/013465
PCT Pub. Date: Feb. 2, 2012

(65) Prior Publication Data
US 2013/0208229 A1 Aug. 15, 2013

(30) Foreign Application Priority Data

Jul. 27, 2010 (IT) .............................. PD2010A0237

(51) Int. Cl.
*G02C 11/08* (2006.01)
*A61F 9/02* (2006.01)
*G02C 5/12* (2006.01)
*G02C 5/14* (2006.01)

(52) U.S. Cl.
CPC ................ *G02C 11/08* (2013.01); *A61F 9/028* (2013.01); *G02C 5/12* (2013.01); *G02C 5/14* (2013.01)

(58) Field of Classification Search
CPC ............ G02C 5/12; G02C 5/14; G02C 5/143; G02C 11/08; A61F 9/028
USPC .................. 351/62, 111, 123, 136; 2/435–437
See application file for complete search history.

(56) References Cited

U.S. PATENT DOCUMENTS

| 4,414,693 A | 11/1983 | Brody |
| 4,692,369 A * | 9/1987 | Nomi ............................ 428/198 |
| 5,363,512 A | 11/1994 | Grabos, Jr. et al. |

(Continued)

FOREIGN PATENT DOCUMENTS

| CN | 2509596 Y | 9/2002 |
| CN | 1782784 A | 6/2006 |

(Continued)

OTHER PUBLICATIONS

International Search Report Issued Nov. 17, 2011 in PCT/EP11/061434 Filed Jul. 6, 2011.

(Continued)

*Primary Examiner* — Huy K Mai
(74) *Attorney, Agent, or Firm* — Oblon, McClelland, Maier & Neustadt, L.L.P.

(57) ABSTRACT

A frame for glasses, masks for professional or sports use, adapted to support at least one corrective and/or protective lens in a position which during use is located in front of the ocular region of the user, the frame including at least one through opening which is open toward the skin of the user who is wearing it, and at least one waterproof and vapor-permeable functional arranged so as to obstruct in a vapor-permeable manner the at least one opening to allow vapor permeation of the skin of the user, preventing a return of condensation toward the skin.

10 Claims, 3 Drawing Sheets

(56) References Cited

U.S. PATENT DOCUMENTS

| | | | |
|---|---|---|---|
| 5,517,700 A | * | 5/1996 | Hoffman .......................... 2/428 |
| 5,542,130 A | | 8/1996 | Grabos, Jr. et al. |
| 2002/0126253 A1 | * | 9/2002 | Wu .............................. 351/123 |
| 2009/0100577 A1 | | 4/2009 | Kobayashi et al. |

FOREIGN PATENT DOCUMENTS

| | | |
|---|---|---|
| CN | 201181363 Y | 1/2009 |
| EP | 2 044 912 | 4/2009 |

OTHER PUBLICATIONS

Combined Georgian Office Action and Search Report issued Mar. 31, 2014, in Georgian Patent Application No. AP 2011 013010 with English translation.

Combined Chinese Office Action and Search Report issued Jul. 25, 2014 in Patent Application No. 201180036662.9 (with English language translation).

* cited by examiner

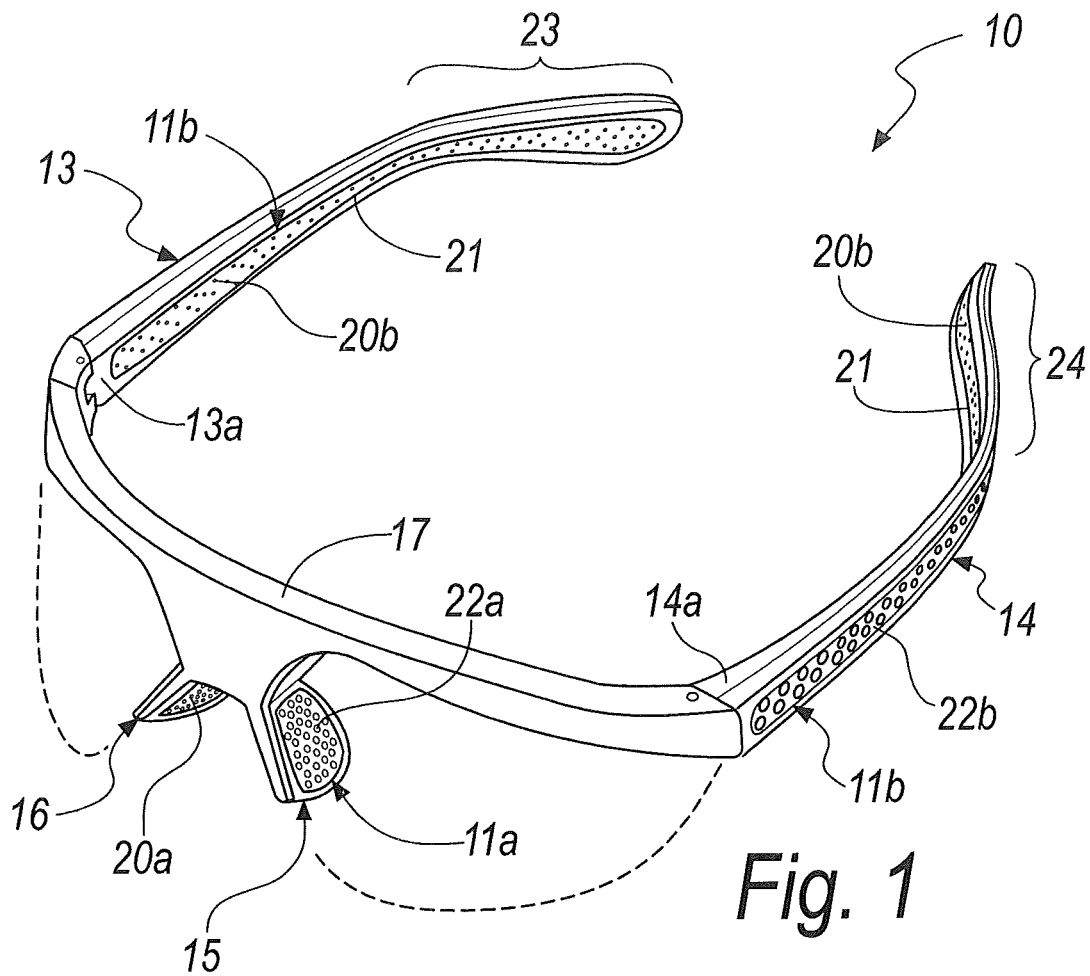
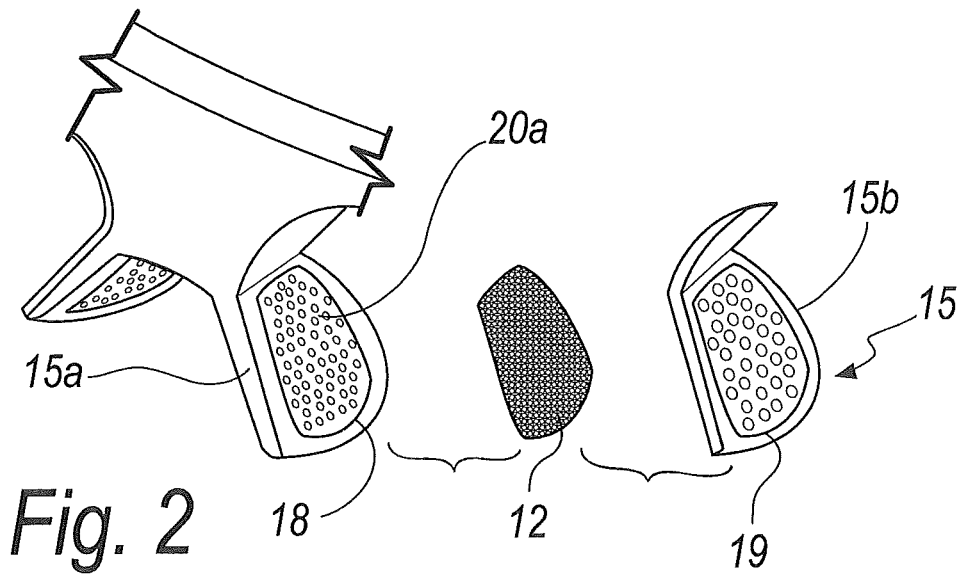
Fig. 1
Fig. 2

FRAME FOR GLASSES, MASKS FOR PROFESSIONAL OR SPORTS USE, AND THE LIKE

TECHNICAL FIELD

The present invention relates to a frame for glasses, masks for professional or sports use, and the like.

BACKGROUND ART

Currently, glasses are commonly used in a large number of applications in order to improve the sight of the user, by correcting imperfections due to refractive defects or shortcomings in ocular functionality, to protect the eyes from the rays of the sun, to help to maintain visibility, which might be compromised by atmospheric conditions, such as rain or snow, or to protect the eyes from the work environment.

Generally, glasses and/or sunglasses are composed of a lens supporting frame that comprises two earpieces, also known as temples, which are connected in an articulated or flexible way to a front for supporting the lenses, which is provided in one-piece frame models.

In three-part frame models, the earpieces are articulated or flexibly connected to two corresponding end pieces, which are adapted to connect with the lenses, which are interconnected by the bridge that supports the nose pieces for resting on the nose of the user.

Moreover, protective masks are currently known which have a supporting rimmed frame for a lens adapted to shield the ocular region of the user from severe weather conditions, for example in masks for sports use, or from the work environment.

An elastic strap is generally associated with the rimmed frame and is adapted to hold the mask firmly in position, once it has been put on by the user to shield the eye region.

Currently, protective mask models of the binocular type, i.e., that have two distinct lenses instead of a single lens, are also known.

In particular, in the field of masks for sports use or work use, great attention has always been paid to devising solutions aimed at increasing the phenomenon of ventilation, i.e., the circulation of air inside the mask, in order to prevent fogging of the lenses.

In the state of the art there are several inventions that have small perforations or slots defined in the lenses or in the upper, lower or lateral portions of the frame, so that air circulates between the mask and the ocular region of the user who is wearing it, flowing over the inner face of the lens in order to reduce its likelihood of fogging.

For example, U.S. Pat. No. 6,009,564 and U.S. Pat. No. 5,542,130 disclose pluralities of openings provided in the front and/or upper portion of a mask frame of the sports type or work type, which however can be obstructed easily by snow or sand during the use in hostile environmental or weather conditions.

Moreover, in case of rain, such openings allow the passage of water inside the mask, fully to the disadvantage of its convenience and effectiveness of use.

Moreover, substantially all currently known frame types, both for eyeglasses and sunglasses, with earpieces and a front or in three parts, as well as rimmed frames for masks, suffer the drawback of substantially preventing vapor permeation of the skin in the regions where they make contact with the skin of the user, particularly for the resting contact.

This drawback is all the more relevant based on the observation that the forehead and the regions adjacent to it are particularly rich in sweat glands.

Therefore, the very areas of the face that are covered by glasses or by a mask are particularly relevant in the essential biological function of sweating, which therefore must be protected by ensuring correct vapor permeation in order to prevent discomfort to the user.

In fact, as is known to people who wear eyeglasses, sunglasses or a mask for sports use or for protection, a bothersome stagnation of sweat originates in the regions of contact between the frame and the skin of the user.

The sweat formed thereat, since its evaporation is hindered, indeed remains directly on the skin and condenses on the frame.

Such phenomenon is particularly conspicuous in goggles of the sports or protective type; in fact, vapor permeation through goggles is almost completely prevented in them.

Moreover, if the frame is not properly cleaned from the sweat and from the greasy substances that it carries, deposits may form over time which are the ideal culture medium for the growth of colonies of pathogenic microorganisms, such as fungi and bacteria, which multiply rapidly and can cause eye infections.

DISCLOSURE OF THE INVENTION

The aim of the present invention is to provide a frame for glasses, masks for professional use or sports use, and the like, that makes it possible to overcome the drawbacks and limitations of conventional frames, in that it is vapor-permeable.

Within this aim, an object of the invention is to provide a frame that allows to prevent the stagnation on the skin of the user of condensation of sweat that has permeated through the skin.

Another object of the invention is to provide a frame that makes it possible to limit greatly, with respect to conventional frames, the risk of proliferation of harmful bacterial colonies on the skin of the user at the regions covered by the frame.

Another object of the invention is to devise vapor-permeable frames that can be provided in different models for use in the field of eyeglasses or for protection against the sun or in the field of protective masks to be used in environments that are aggressive for the biological balance of the ocular region of the user, as well as for protection against wind, against cold or against intense thermal radiation, or for protection against free particles such as grains of sand or sparks or the like.

This aim, as well as these and other objects that will become better apparent hereinafter are achieved by a frame for glasses, masks for professional or sports use, and the like, adapted to support at least one corrective and/or protective lens in a position which during use is located in front of the ocular region of the user, characterized in that it is provided with at least one through opening which is open toward the skin of the user who is wearing said frame, at least one waterproof and vapor-permeable functional insert being provided which is arranged so as to obstruct in a vapor-permeable way said at least one opening in order to allow the vapor permeation of the skin of the user, preventing a return of condensation toward the skin.

BRIEF DESCRIPTION OF THE DRAWINGS

Further characteristics and advantages of the invention will become better apparent from the description of preferred but not exclusive embodiments of the frame according to the invention, illustrated by way of non-limiting example in the accompanying drawings, wherein:

FIG. 1 is a perspective view of a frame according to the invention, in a first embodiment;

FIG. 2 is an enlarged-scale exploded perspective view of a detail of the frame of FIG. 1 according to the invention;

WAYS OF CARRYING OUT THE INVENTION

Figure 3:
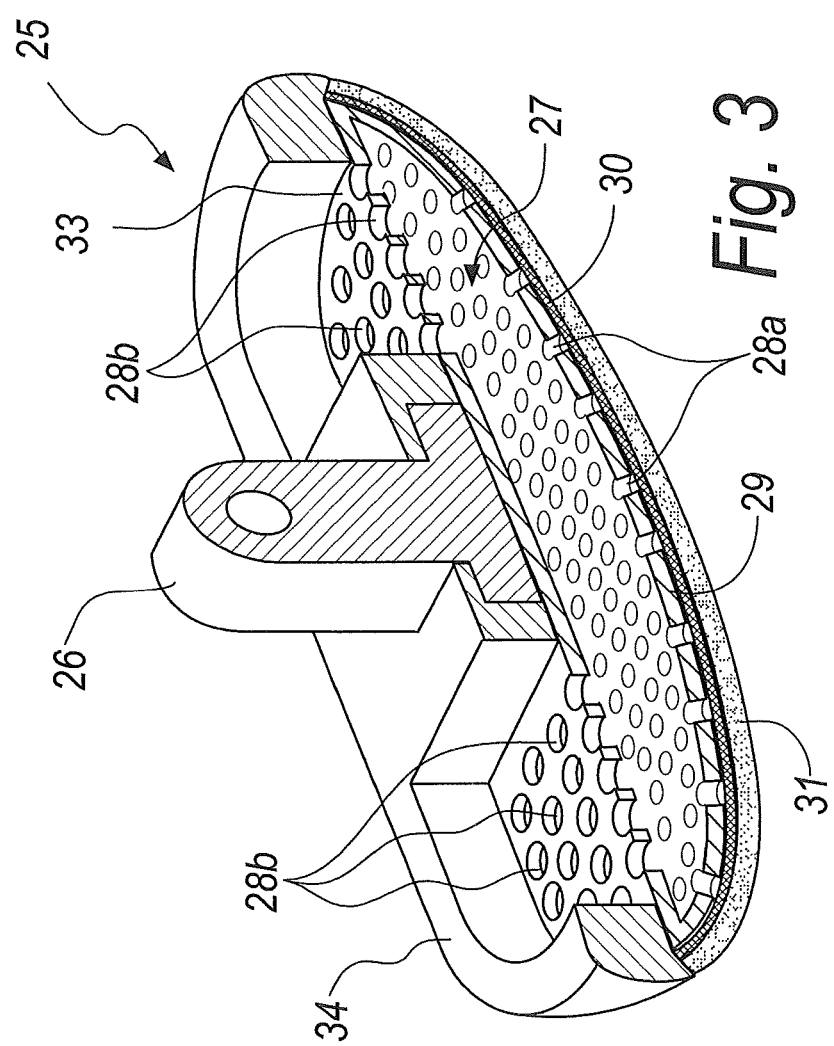
FIG. 3 is an enlarged-scale sectional perspective view of a detail of a constructive variation of the frame according to the invention.

With particular reference to the figures, the reference numeral 10 generally designates a frame for glasses which is adapted to support two corrective and/or protective lenses in a position which, during use, is located in front of the ocular region of the user, in a manner known per se.

According to the invention, the frame 10 has the peculiarity that it has a plurality of through openings 11a and 11b, which are open toward the skin of the user who is wearing the frame 10, waterproof and vapor-permeable functional inserts being provided which are arranged so as to obstruct in a vapor-permeable way the corresponding openings 11a and 11b, so as to allow through them the vapor permeation of the skin of the user, at the same time preventing a return of condensation toward the skin.

With reference to FIG. 2, one of said functional inserts is shown schematically and is designated by the reference numeral 12.

In particular, the functional inserts are conveniently connected so as to provide a waterproof seal to the walls that delimit the openings 11a and 11b that they close.

For example, as illustrated by way of non-limiting example in FIGS. 1 and 2, earpieces 13 and 14 and nose pieces 15 and 16 are conveniently provided in two joined parts, between which the functional inserts are inserted, as described extensively hereinafter.

In particular, FIG. 2 illustrates by way of non-limiting example the structure of the first nose piece 15 of the nose pieces 15 and 16, the structure of the second nose piece 16 and of the earpieces 13 and 14 being substantially similar and therefore not being further described.

Advantageously, the first nose piece 15 is open through its thickness in order to define a nasal vapor permeation opening 11a of openings 11a and 11b, and is conveniently defined by a first part 15a, which is jointly connected to a front 17 of the frame 10, and by a second part 15b, which is joined to the first part 15a, the functional insert 12 shaped so as to conform to them being interposed between them.

The parts 15a and 15b conveniently have an annular structure, being provided with two corresponding windows 18 and 19 which, when the parts 15a and 15b are joined, cooperate to define the nasal vapor permeation opening 11a.

The first part 15a is conveniently joined to the second part 15b by adhesive bonding, so that a peripheral region of the functional insert 12 is joined hermetically to the parts 15a and 15b, the functional insert 12 remaining mostly free from the adhesive used for bonding, in order to preserve its vapor permeability through windows 18 and 19 which, during use, define the nasal vapor permeation opening 11a.

In alternative embodiments of the invention, for example, the parts can be joined by high-frequency welding or overmolding of one over the other with a functional insert inserted between them.

Advantageously, absorbent and vapor-permeable elements 20a and 20b are provided which cover the inner face of the functional inserts, the inner face being directed, during use, toward the skin of the user.

Absorbent and vapor-permeable elements 20a and 20b are conveniently capable of absorbing sweat and of preventing its retention by impregnation.

In particular, a first one 20a of the absorbent and vapor-permeable elements 20a and 20b is shaped so as to be accommodated in the first one 18 of the windows 18 and 19, which is open through the first part 15a of the first nose piece 15.

In a substantially equivalent manner, second elements 20b of the absorbent and vapor-permeable elements 20a and 20b are shaped so as to be accommodated in windows 21 which are extended longitudinally and are open in the inner parts 13a and 14a of the earpieces 13 and 14, in order to define an inner part of temporal vapor permeation openings 11b of the openings 11a and 11b.

More particularly, the absorbent and vapor-permeable elements 20a and 20b are conveniently made of a material selected among felt,
nonwoven fabric,
mesh of polymeric material,
microfiber,
leather,
and the like.

The frame 10 conveniently further comprises vapor-permeable and/or perforated covering elements 22a and 22b, which substantially cover the outer face of the functional inserts, such outer face being opposite with respect to the face directed toward the skin of the user who is wearing the frame 10.

In general, depending on the implementation requirements of a frame according to the invention, such frame comprises earpieces provided with transversely through openings, which openings are open through at least the free end portions, which free end portions are adapted to face and/or abut against the skin of the user, and are designated by way of non-limiting example by the reference numerals 23 and 24 in FIG. 1.

In the frame 10, described herein by way of non-limiting example, the transverse through openings are conveniently provided by the temporal vapor permeation openings 11b.

Moreover, depending on the contingent requirements, the covering elements may have a mesh-like or grid-like structure.

In a constructive variation of a frame according to the invention, the frame can comprise nose pieces which are articulated so as to adapt to the nose of the user on which they are adapted to support the frame.

FIG. 3 illustrates by way of non-limiting example an articulated nose piece according to a further embodiment, generally designated by the reference numeral 25.

The articulated nose piece 25 conveniently comprises an articulation portion 26 adapted to be articulated to the nasal part of a frame according to the invention, in a manner which is known per se and therefore not further described.

Moreover, the nose piece 25 preferably comprises a framework 27 which is jointly connected to the articulation portion 26 and is provided with openings 28a and 28b which, during the use of the frame, connect to the surrounding environment, through the framework 27, the skin of the user on which the articulated nose piece 25 rests at a resting contact wall 29 of the framework 27, which is conveniently ergonomically shaped.

A waterproof and vapor-permeable functional insert, designated in FIG. 3 by the reference numeral 30, advantageously covers first nasal vapor permeation openings 28a, of the openings 28a and 28b, which are open through the resting contact wall 29, closing them with a waterproof seal for example by perimetric adhesive bonding to the resting contact wall 29.

The functional insert 30 thus allows, through the first nasal vapor permeation openings 28a, the vapor permeation of the user's skin on which the nose piece 25 rests during use and at the same time prevents the return of condensation toward the skin.

Conveniently, an absorbent and vapor-permeable element is also provided, designated in FIG. 3 by the reference numeral 31, which covers the functional insert 30 and is capable of absorbing sweat and preventing retention by impregnation.

Moreover, the framework 27 is conveniently made of polymeric material and advantageously has a box-like structure, which defines a vapor-permeable chamber delimited by the resting contact wall 29 and by a rear wall 33 of the framework 27, which conveniently has the second nasal vapor permeation openings 28b of the openings 28a and 28b.

Conveniently, the framework 27 is made of absorbent and vapor-permeable material, such as for example felt, nonwoven fabric and the like.

Preferably, the rear wall 33 is covered with a finishing element 34, made of soft material such as for example silicone, which is conveniently provided with through holes in order to leave free the second nasal vapor permeation openings 28b.

In a constructive variation of the nose piece 25, not further described herein, the waterproof and vapor-permeable functional insert can have a considerable thickness, such as to give it an independent resistance to the stresses that can be experienced during correct use of the frame that incorporates it, and thus lack the absorbent and vapor-permeable element.

In such constructive variation, the waterproof and vapor-permeable functional insert is preferably made of a polymeric material that is extruded in a single layer with a substantial thickness or obtained by lamination of a plurality of superimposed layers, or again obtained by lamination of a plurality of superimposed layers with an additional insert provided between them in order to obtain a single cohesive element.

The polymeric material is advantageously selected among polytetrafluoroethylene, PTFE, polyurethane, PU, polyester, PES, polypropylene, PP, polyethylene, PE, and the like.

A functional insert with such characteristics can be obtained by using a single layer, for example made of PTFE material, with a thickness preferably comprised between 0.1 mm and 3.0 mm, or a multilayer, for example made of expanded PTFE material, with a thickness preferably within the 0.1 mm-5.0 mm range.

As an alternative, a sintered and porous polymeric composite material commonly known by the trade name POREX® can also be used advantageously.

Depending on the contingent implementation requirements of the invention, different methods of construction of the nose piece 25 can be selected.

In particular, for example, the functional insert 30 is conveniently hot-preformed in a provided mold, so as to make it conform to the framework 27, to which it is subsequently associated, preferably by perimetric adhesive bonding.

As an alternative, in a further constructive method of the nose piece of a frame according to the invention, the framework of the nose piece is shaped like a gondola and conveniently made of absorbent and vapor-permeable material.

In this construction method, the framework is made of vapor-permeable material, such as for example felt, and thus lacks the openings and the vapor permeation chamber, since their function, i.e., to allow the passage of water vapor through the framework, is performed equivalently by the vapor-permeable structure of the framework.

The functional insert is conveniently overmolded while hot on the vapor-permeable framework, for example by arranging, in an appropriate hot mold, the framework and the functional insert, and by actuating the mold, which thus makes the functional insert conform to the framework, joining them integrally.

Figure 4:
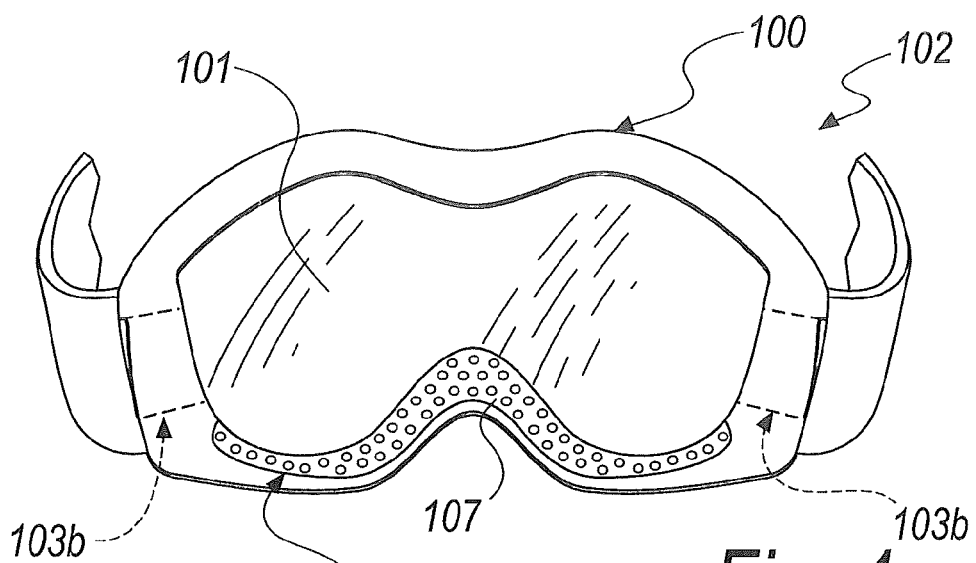
FIG. 4 is a front view of a frame according to the invention, in a second embodiment.
Figure 5:
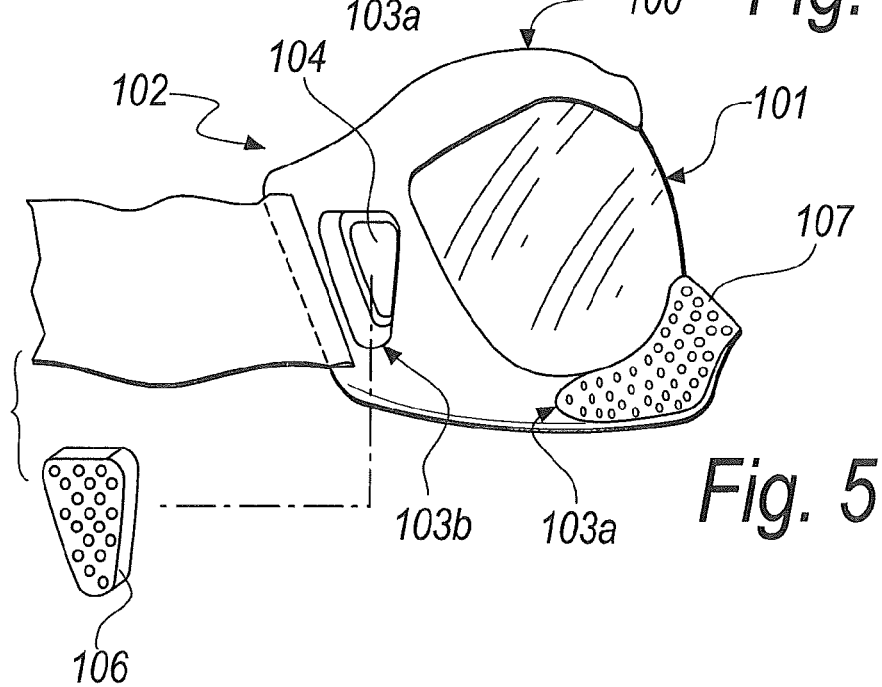
FIG. 5 is a side view of the frame of FIG. 4 according to the invention.
Figure 6:
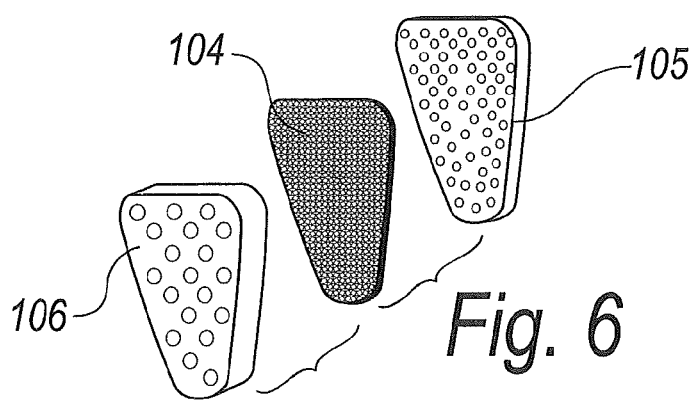
FIG. 6 is an exploded perspective view of a detail of the frame according to the invention, provided in said second embodiment.

With particular reference to FIGS. 4, 5 and 6, a frame 100 according to the invention, in a second embodiment, has a rimmed structure for supporting a lens 101 in order to define a mask 102.

According to the invention, the frame 100 is provided with through openings 103a and 103b which are open toward the skin of the user who is wearing it.

Waterproof and vapor-permeable functional inserts are arranged so as to obstruct in a vapor-permeable manner the openings 103a and 103b in order to allow vapor permeation of the skin of the user, preventing a return of condensation toward the skin.

Advantageously, the functional inserts are connected so as to provide a waterproof seal to the walls that delimit openings 103a and 103b that they close.

Conveniently, the openings 103a and 103b comprise
a nasal vapor permeation opening 103a, which is provided at a nasal part of the frame 100 and is designed to rest on the nose of the user and
temporal vapor permeation openings 103b, which are provided at a temporal part of the frame 100, which is designed to face the temporal region of the user who is wearing it and/or to be rested thereon.

The temporal vapor permeation openings 103b are conveniently closed by a first functional insert 104 of the functional inserts, which is conveniently covered, on its face that is internal to the mask 102, by an absorbent and vapor-permeable element 105, such inner face being directed, during use, toward the skin of the user.

The absorbent and vapor-permeable element 105 is conveniently capable of absorbing sweat and of preventing retention by impregnation and is preferably made of a material selected among
felt,
nonwoven fabric,
mesh of polymeric material,
microfiber,
leather,
and the like.

Moreover, the frame 100 has advantageously the first functional insert 104 protected by a perforated or vapor-permeable covering element 106 in substantially equivalent constructive variations.

Conveniently, the covering element 106 substantially covers the outer face of the first functional insert 104, such outer face being opposite with respect to the face directed toward the skin of the user who is wearing the frame 100.

In the same way, which therefore is not described and illustrated further in the figures, a second functional insert of the functional elements is provided, which encloses the nasal vapor permeation opening 103a.

Advantageously, the second functional insert is covered, on its face that is internal to the mask 102, by an absorbent and vapor-permeable element, not shown in the accompanying figures, such inner face being directed, during use, toward the skin of the user, the absorbent and vapor-permeable element being conveniently capable of absorbing sweat and of preventing its retention by impregnation and being preferably made of a material selected among felt,
    nonwoven fabric,
    mesh of polymeric material,
    microfiber,
    leather,
    and the like.

Moreover, in FIGS. 4 and 5 the reference numeral 107 designates a covering element for the second functional insert, which is substantially similar to the covering element 106 and therefore is not further described.

In a constructive variation of the frame according to the invention, which is adapted to provide a mask, not further illustrated herein, the waterproof and vapor-permeable functional insert may have a considerable thickness, such as to give it an independent resistance to the stresses that can be experienced during correct use of the frame that incorporates it, and may thus lack the absorbent and vapor-permeable element.

Moreover, in further constructive variations, advantageously the frame according to the invention, which is adapted to define a mask, has the openings, sealed in a waterproof and vapor-permeable way by functional inserts, substantially at all the parts directly in contact with the skin of the user, particularly, on the entire contour of the frame adapted to be rested against the face of the user perimetrically to his ocular region, the functional inserts having preferably a considerable thickness, i.e., such as to give them an independent resistance to the stresses that can be experienced during the correct use of the frame that incorporates them.

The terms waterproof and vapor-permeable designate the quality of the functional inserts of being impermeable to water, particularly to sweat, in the liquid state, i.e., condensed, and permeable to water vapor.

In general, depending on the contingent requirements of execution of a frame according to the invention, the frame has at least one through opening which is open toward the skin of the user who is wearing it, at least one waterproof and vapor-permeable functional insert being provided which is arranged so as to obstruct in a vapor-permeable manner the opening in order to allow vapor permeation of the skin of the user, preventing a return of condensation toward said skin.

In a substantially equivalent manner, the at least one opening may be replaced by at least one vapor-permeable region of the frame.

Advantageously, the functional inserts comprise, depending on the contingent requirements of execution of the invention, selectively among at least one waterproof and vapor-permeable membrane which is thin, i.e., for example has a thickness substantially comprised between 10 microns and 100 microns, and is made of polymeric material,
    at least one waterproof and vapor-permeable membrane which is thick, i.e., for example has a thickness substantially comprised between 0.1 mm and 5 mm, made of polymeric material, such thick membrane being selectively either a single body or multilayer and cohesive, and the extruded polymeric material being moreover selectively either expanded or not expanded,
    at least one layer made of sintered and porous composite polymeric material, such for example the product commercially known as POREX®.

In particular, the polymeric material is advantageously selected among polytetrafluoroethylene, PTFE,
    polyurethane, PU,
    polyester, PES,
    polypropylene, PP,
    polyethylene, PE,
    and the like.

Depending on the contingent requirements of execution of the invention, the functional inserts comprise at least one layer made of such membrane, for example they may be made as a single body of said polymeric material, or may be made as a cohesive layering of a plurality of layers of the membrane, or also may be made by one of the membranes, covered, for protection, by vapor-permeable layers, or, in a particularly preferred solution, the functional inserts may be made of polytetrafluoroethylene, PTFE, as a single body, which has a thickness advantageously comprised between 0.1 mm and 3 mm, or
    layered, which has a thickness conveniently comprised between 0.1 mm and 5 mm.

Moreover, depending on the contingent requirements of execution of the invention, the functional inserts may comprise a plurality of layers made of PTFE, or equivalent, with the interposition of a porous material that is permeable to water vapor, such as for example nonwoven fabrics, nets, meshes and other porous films, composed of polyolefins, nylon, polyester, aramid fibers or fluoropolymers.

In practice it has been found that the invention achieves the intended aim and objects, by providing a frame for glasses, masks for professional or sports use, and the like, that makes it possible to overcome the drawbacks and limitations of conventional frames, in that it is vapor-permeable.

In particular, a frame according to the invention makes it possible to prevent the stagnation, on the skin of the user, of condensed sweat that has permeated through the skin; in fact, sweat, in the form of vapor, passes through the openings of the frame, permeating through the functional inserts that close them.

Even in the case of condensation of the sweat permeated through the functional inserts toward the outside of the frame, the inserts prevent its return into contact with the skin because they are waterproof and are sealed in a waterproof manner to the frame.

A frame according to the invention, moreover, allows to limit greatly, with respect to conventional frames, the risk of proliferation of harmful bacterial colonies on the skin of the user at the regions covered by the frame; in fact, it allows the vapor permeation of the sweat produced by the skin, preventing its stagnation and therefore the formation of seats of bacterial proliferation in contact with the skin.

Moreover, vapor-permeable frames according to the invention may be provided in the most disparate models in order to be suitable for the contingent requirements of use; for example, they may be adapted to the use in the field of eyeglasses and/or sunglasses, being provided in a single piece, optionally in the shape known as "rimless", or in three pieces.

As an alternative, frames according to invention can be provided in order to form protective masks to be used in environments that are aggressive for the biological balance of the ocular region of the user, such as for protection against wind, cold or against intense thermal radiations or for protection against free particles such as grains of sand or sparks or the like.

The invention thus conceived is susceptible of numerous modifications and variations, all of which are within the scope of the appended claims; all the details may further be replaced with other technically equivalent elements.

In practice, the materials used, so long as they are compatible with the specific use, as well as the contingent shapes and dimensions, may be any according to requirements and to the state of the art.

The disclosures in Italian Patent Application No. PD2010A000237 from which this application claims priority are incorporated herein by reference.

Where technical features mentioned in any claim are followed by reference signs, those reference signs have been included for the sole purpose of increasing the intelligibility of the claims and accordingly such reference signs do not have any limiting effect on the interpretation of each element identified by way of example by such reference signs.

The invention claimed is:

1. A frame for glasses, masks for professional or sports use, adapted to support at least one corrective and/or protective lens in a position which during use is located in front of the ocular region of a user, comprising:
   at least one through opening which is open toward the skin of the user who is wearing said frame, wherein the at least one through opening extends through the frame; and
   at least one waterproof and vapor-permeable functional insert arranged so as to obstruct in a vapor-permeable manner the at least one opening to allow vapor permeation of the skin of the user to an external environment, preventing a return of condensation toward the skin.

2. The frame according to claim 1, wherein said at least one functional insert includes at least one layer of a membrane made of polymeric material selected among:
   polytetrafluoroethylene, PTFE,
   polyurethane, PU,
   polyester, PES,
   polypropylene, PP, and
   polyethylene, PE.

3. The frame according to claim 1, wherein said at least one functional insert is connected to provide a waterproof seal to walls that delimit the at least one opening that the functional insert closes.

4. The frame according to claim 1, further comprising at least one absorbent and vapor-permeable element, which covers an inner face of the at least one functional insert, the inner face being directed, during use, toward the skin of the user, and the absorbent and vapor-permeable element being capable of absorbing sweat and preventing its retention by impregnation.

5. The frame according to claim 4, wherein the absorbent and vapor-permeable element is made of a material selected among:
   felt,
   nonwoven fabric,
   mesh of polymeric material,
   microfiber, and
   leather.

6. The frame according to claim 1, further comprising at least one vapor permeable and/or perforated covering element, which substantially covers an outer face of the at least one functional insert, the outer face being opposite with respect to the face directed toward the skin of the user who is wearing said frame.

7. The frame according to claim 1, wherein the at least one through opening comprises at least one through opening for nasal vapor permeation, which is provided at a nose part of the frame that is configured for resting on the nose of the user.

8. The frame according to claim 1, wherein the at least one through opening comprises at least one through opening for temporal vapor permeation, which is provided at a temporal part of the frame, which is configured to face a temporal region of the user who is wearing the frame and/or to be rested thereon.

9. The frame according to claim 1, further comprising two earpieces for resting on ears of the user, the at least one through opening comprising openings that pass transversely through the earpieces, the openings being open through at least free end portions of the earpieces and being adapted to face and/or abut against the skin of the user.

10. A frame for glasses, masks for professional or sports use, adapted to support at least one corrective and/or protective lens in a position which, during use, is in front of the ocular region of a user, comprising:
   at least one region which is vapor-permeable toward the skin of the user who is wearing said frame; and
   at least one waterproof and vapor-permeable functional insert arranged so as to seal in a waterproof and vapor-permeable manner the at least one vapor-permeable region to allow vapor permeation of the skin of the user to an external environment, preventing a return of condensation toward the skin.

* * * * *